United States Patent [19]
Miyata et al.

[11] Patent Number: 5,647,127
[45] Date of Patent: Jul. 15, 1997

[54] MANUFACTURING PROCESS OF COIL

[75] Inventors: Naohiko Miyata, Nagoya; Masashi Momota, Ohmiya; Kazuyuki Shimada, Seto, all of Japan

[73] Assignee: Asahi Intell Co. Ltd., Japan

[21] Appl. No.: 491,429

[22] Filed: Jun. 16, 1995

Related U.S. Application Data

[62] Division of Ser. No. 164,221, Dec. 7, 1993, Pat. No. 5,520,194.

[51] Int. Cl.$^6$ ........................................ B21F 35/00
[52] U.S. Cl. ........................ 29/896.9; 228/156; 228/265
[58] Field of Search ........................ 29/896.9; 228/156, 228/265; 128/657, 772

[56] References Cited

U.S. PATENT DOCUMENTS

| | | |
|---|---|---|
| 4,020,829 | 5/1977 | Willson et al. . |
| 4,884,579 | 12/1989 | Engelson . |
| 4,917,285 | 4/1990 | Shosie . |
| 4,922,924 | 5/1990 | Gambale et al. . |
| 5,144,959 | 9/1992 | Gambale et al. . |
| 5,174,302 | 12/1992 | Palmer . |

FOREIGN PATENT DOCUMENTS

92/19663  10/1993  WIPO .

*Primary Examiner*—P. W. Echols
*Attorney, Agent, or Firm*—Fulbright & Jaworski

[57] ABSTRACT

A guide wire for medical purposes having a proximal section and a distal section and formed by inserting all or a portion of a slender and flexible shaft into a coil and fixing the shaft to the coil, wherein the coil is a multiple-wire coil consisting of at least two pieces of wire, at least one of these pieces of wire is made of a material which is opaque against radioactive rays such as X-rays, and a portion of the coil closer to the distal section of the shaft is a single-wire coil consisting of only a composite wire made of the radiopaque material.

2 Claims, 6 Drawing Sheets

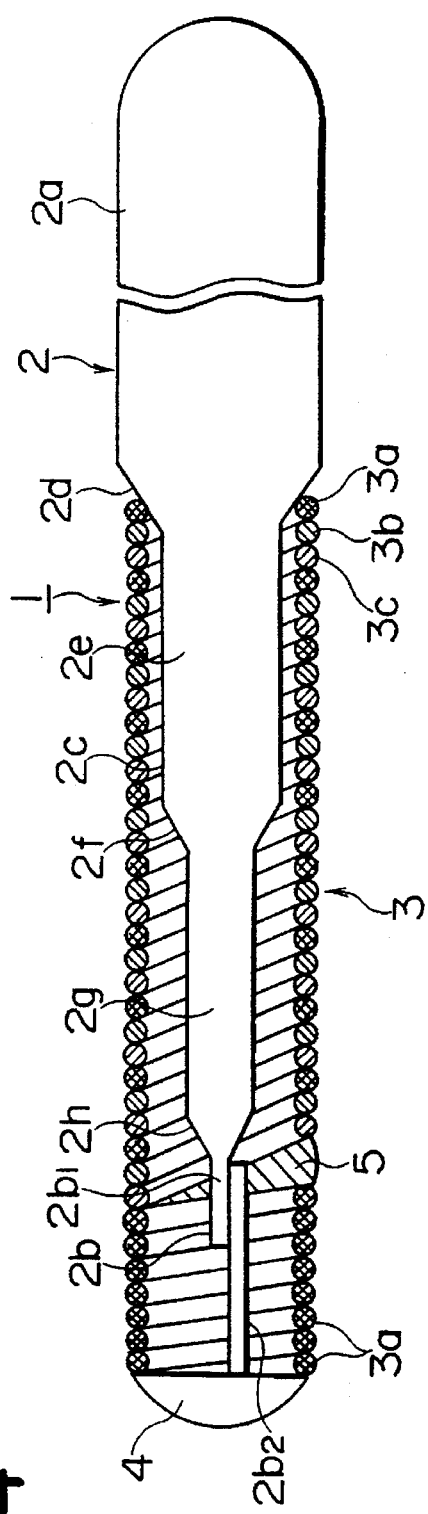
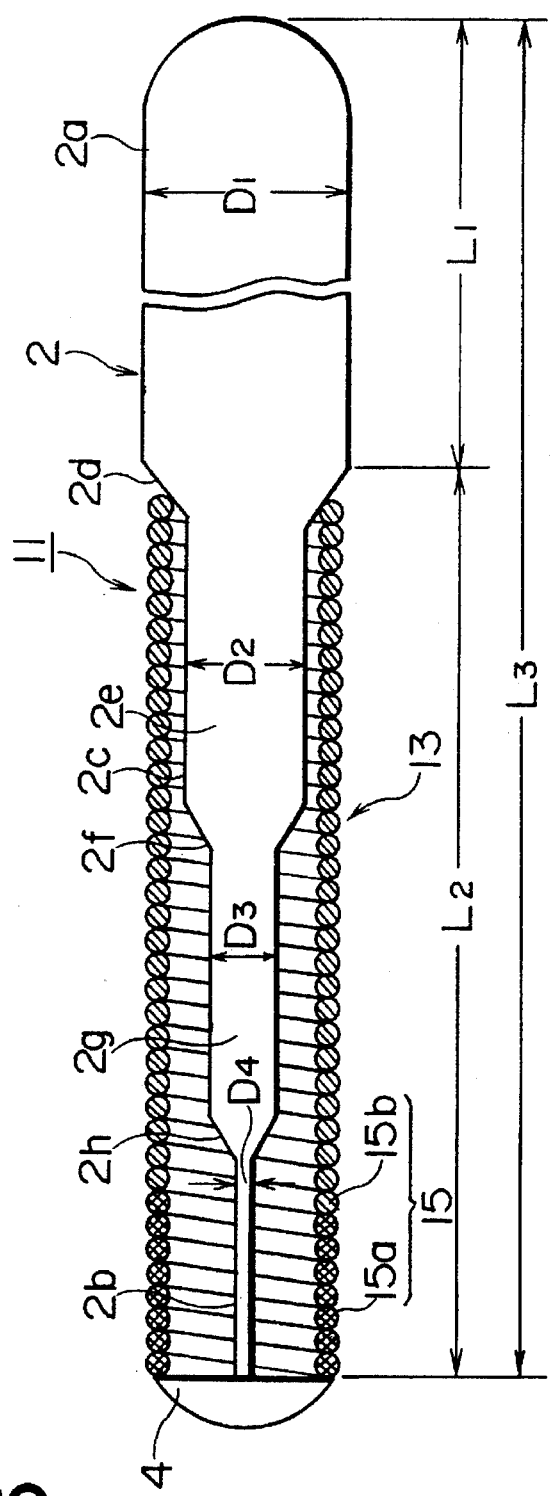
FIG. 4
FIG. 5

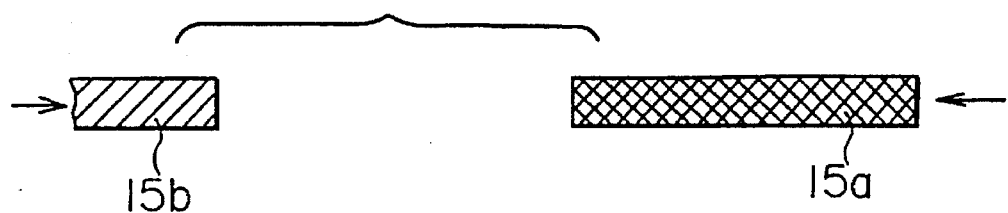
FIG. 6 (A)
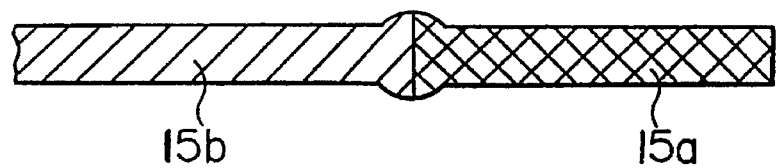
FIG. 6(B)
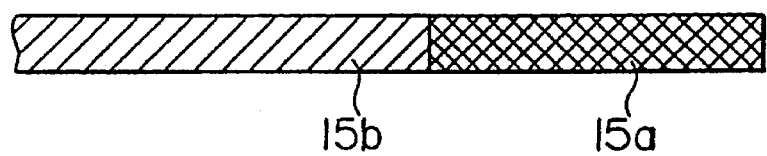
FIG. 6(C)
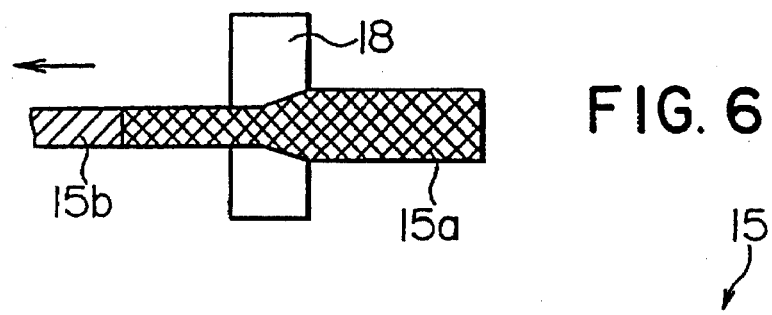
FIG. 6(D)
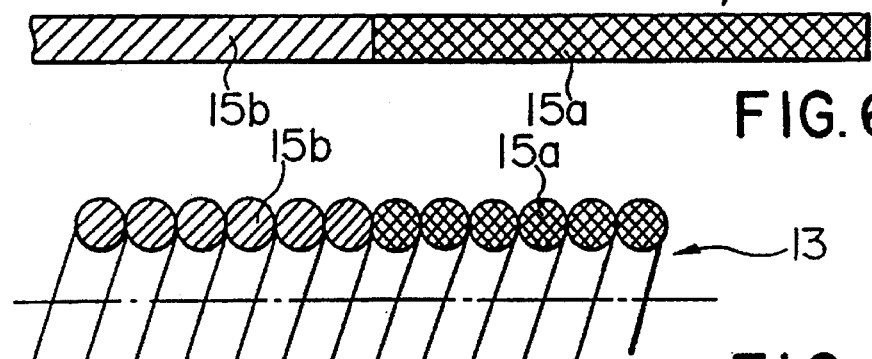
FIG. 6(E)
FIG. 6(F)

MANUFACTURING PROCESS OF COIL

This is a division of application Ser. No. 08/164,221 filed Dec. 7, 1993, now U.S. Pat. No. 5,520,194.

FIELD OF THE INVENTION

The present invention relates to a guide wire used for introducing a catheter into a blood vessel system, especially into a human heart blood vessel system, and a manufacturing process of a coil constituting the guide wire.

BACKGROUND OF THE INVENTION

For the purpose of introducing a catheter into a blood system for angiography, conventionally a guide wire has been used to more safely and more accurately carry out the introduction. The guide wire is effective in situations involving relatively thick blood vessels or those having relatively simple branches or bending in a relatively simple form. It is, however, very difficult to carry the catheter into a depth of a blood vessel branching very minutely, such as a coronary of a human heart and especially for substantially stenosed portions thereof, and a guide wire based on a completely different concept is required. Especially in the case of guide wire used for a catheter for blood vessels forming in substantially stenosed sections, it is essential that a portion near a tip of the guide wire should be opaque against radioactive rays, such as X-rays, in order to accurately detect a stenosed portion. To achieve the object as described above, a guide wire as disclosed, for instance, in Japanese Patent Publication No. 25024/1992 has been proposed.

In the conventional type of guide wire as described above, two pieces of coil are connected to a section near a tip of shaft made of metal having a high twistability, and of the two pieces of coil, the one closer to the tip is made of a radiopaque material so that the guide wire will be provided with high flexibility and high bending capability as well as be easily detected by radioactive rays, through various devices which are introduced. However, in this type of guide wire, two coils made of different materials are artificially coupled and connected by means of screwing or soldering, so particular considerations are required to maintain mechanical safety and strength in the connected section, and in addition, because mechanical characteristics of the connected section become discontinuing when a guide wire passes through a blood vessel having an extremely small curvature, sometimes passage also becomes impossible due to discontinuity of bending radius in this connected section. Namely in FIG. 1A and FIG. 1B, each diagrammatically illustrating the situations where the problem as described occurs, if the connected section 51 of the guide wire 50 is too hard, it can not follow bending of a blood vessel 52 and can not pass through the section (FIG. 1A), and, on the other hand, if the connected section 51 is too soft, it bends and passage becomes impossible (FIG. 1B).

SUMMARY OF THE INVENTION

The present invention was made in the light of circumstances as described above, and it is an object of the present invention to provide a guide wire for medical purposes which has no connection and can pass through even a blood vessel having an extremely small curvature.

A guide wire for medical purposes according to this invention is a guide wire for medical purposes having a proximal section and a distal section, wherein all or a portion of slender and flexible shaft is inserted into and fixed in a coil to achieve the above-described object, the coil is a multiple-wire coil comprising at least two or more pieces of wire, of these pieces of wire at least one piece of wire is made of a radiopaque material, and a portion of the coil closer to the distal section of the shaft is a single-wire coil made of the radiopaque material. In one mode of carrying out this invention, the radiopaque material is made of either an alloy containing platinum as a main component, an alloy containing gold as a main component, an alloy containing tungsten as a main component, or lead.

Furthermore, in another embodiment of the present invention, a portion of single-wire coil consisting of a piece of wire made of the radiopaque material and an edge portion consisting of a different piece of wire are contacted and fixed to each other by means of soldering. Furthermore, in a different embodiment of the present invention, the distal section of the shaft comprises two portions jointed to each other in the axial direction.

A guide wire for medical purposes according to this invention is a guide wire for medical purposes having a proximal section and a distal section, wherein all or a portion of slender and flexible shaft is inserted into and fixed in a coil to achieve the above-described object, the coil is a single-wire one consisting of one composite wire having no connection, and a portion of this coil closer to the distal section of the shaft is made of the material opaque against radioactive rays such as X-rays. In a still different embodiment of the present invention, a composite wire of a coil comprises an inner layer and an outer layer, and a portion of the inner layer closer to the distal section of the shaft is made of radiopaque material, and the outer layer and a portion of the inner layer other than that closer to the distal section of the shaft is made of a radiotransparent material.

In the different embodiment of the present invention, the radiopaque material is made of either an alloy containing platinum as a main component, an alloy containing gold as a main component, an alloy containing tungsten as a main component, or lead.

Namely, in the invention as described above, the coil is a multiple-wire coil consisting of at least two pieces of wire each having no connection or a single-wire coil consisting of a composite wire having no connection, so that the coil has no remarkable irregularity in bending radius when bent like that of a conventional type of guide wire having a connection and the ending ratio is kept at a constant level, so that the coil can easily pass through even a minute blood vessel having an extremely small curvature. Also, as a portion of coil closer to the shaft distal section is made of a radiopaque material, when fluoroscopy is carried out, the section can easily be distinguished from the surrounding minute vessel, and also a position of the guide wire itself can easily be detected. For this reason, a guide wire can easily be passed through even a blood vessel having an extremely small curvature, and is convenient especially when introducing a catheter into a minute blood vessel such as those in a human heart.

Also it is an object of the present invention to provide a coil manufacturing method which makes it possible to produce a coil constituting the guide wire.

In the coil manufacturing method according to the present invention, in order to achieve the object as described above, when producing coils for a guide wire, a piece of wire made of a radiotransparent material and a piece of wire made of a radiopaque material are jointed by soldering one edge section of a piece of wire to an opposing edge section of another piece of wire, and these jointed two pieces of wire are pulled through a die to make them into a composite wire having a smaller diameter, which is manufactured into a coil. In one embodiment of the present invention, when manufacturing a coil for guide wire, a piece of wire made of a radiopaque material is inserted into one side of the thin tubular outer layer made of a radiotransparent material and a piece of wire made of a material which is the same as that of the outer layer is inserted into the other side thereof, and then the complex layer is pulled through a die to form a composite wire having a smaller diameter, which is manufactured into a coil. With these operations, a coil constituting a guide wire can easily be manufactured.

BRIEF DESCRIPTION OF THE DRAWINGS

FIG. 4 is a longitudinal front sectional view of a guide wire illustrating another formation of the shaft, but lacking a portion thereof;

FIG. 5 is a longitudinal front sectional view of a guide wire illustrating another embodiment of the present invention, but lacking a portion thereof;

FIG. 6 is a schematic diagram illustrating a manufacturing process of the coil above;

DETAILED DESCRIPTION OF THE PREFERRED EMBODIMENTS

Figure 2:
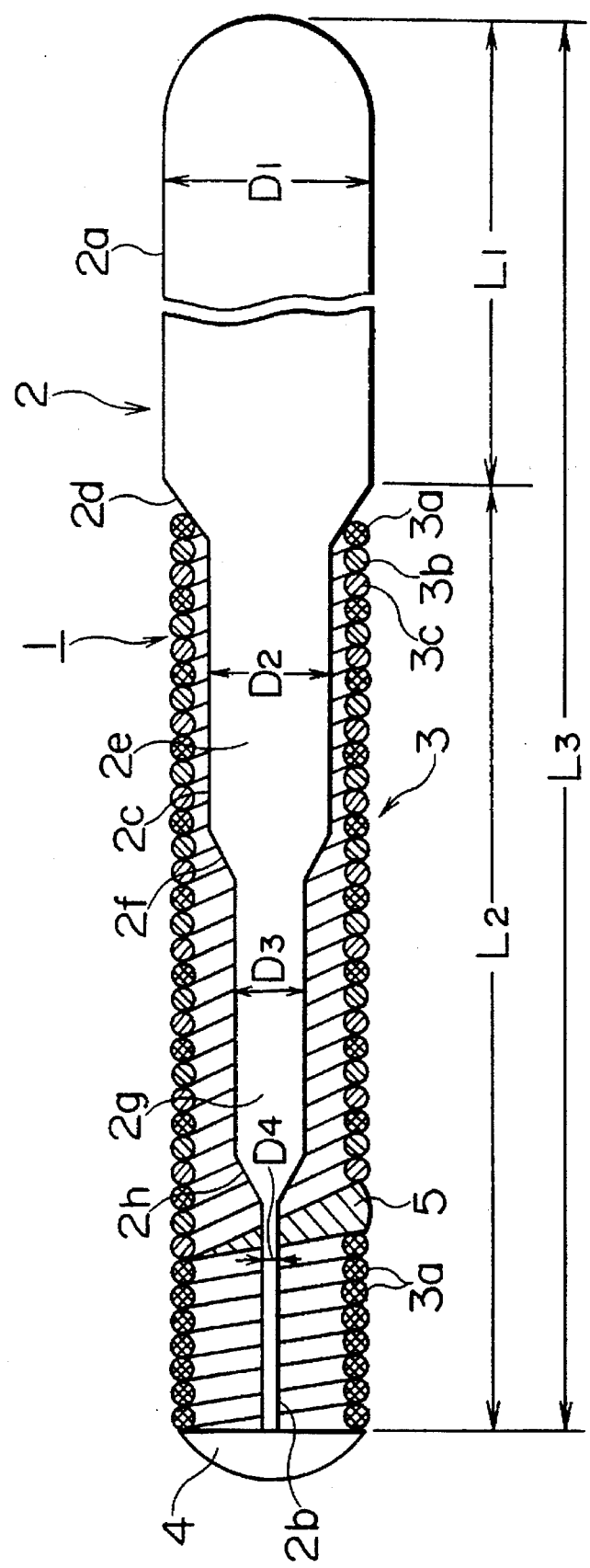
FIG. 2 is a longitudinal front sectional view of a guide wire illustrating an embodiment of the present invention, but lacking a portion thereof.

In FIG. 2, designated at the reference numeral 1 is a guide wire, which comprises a slender and flexible shaft 2 made of such a material as stainless steel, a coil 3, and a plug 4. The shaft 2 comprises a proximal section 2a, a distal section 2b and an intermediate section 2c, and the intermediate section 2c and the distal section 2b are tapered toward the plug 4 by means of grinding. A length $L_1$ of the proximal section 2a of the shaft 2 is 1400 mm, while a length $L_2$ of other portion thereof is 350 mm, so the full length $L_3$ is 1750 mm. The proximal section 2a has a cylindrical form having a diameter $D_1$ of 0.35 mm. The intermediate section 2c comprises a cylindrical form section 2e with the diameter reduced via the tapered section 2d to $D_2$ of 0.19 mm and a cylindrical form section 2g with the diameter reduced via the tapered section 2f to $D_3$ of 0.13 mm, and the cylindrical distal section 2b with the diameter reduced via the tapered section 2h at the tip of this cylindrical section 2g to $D_4$ of 0.05 mm is provided monolithically. At the tip of the distal section 2b is fixed the plug 4 having a roundness toward the tip.

The coil 3 is a multi-stripe one consisting of three pieces of wire each having no connection like that in the conventional type of coil. Of these, a piece of wire 3a is made of a heavy metal such as, for instance, an alloy containing platinum as a main component, an alloy containing gold as a main component, an alloy containing tungsten as a main component, or lead. The other two pieces of wire 3b and 3c are made of a material such as stainless steel, SUS 304, etc., which X-rays can pass through. Also the coil 3 is a single-wire one consisting of only piece of wire 3a in the portion closer to the distal section 2b of the shaft 2 because the pieces of wire 3b and 3c are gradually reduced and finally disappear in this portion. As the pieces of wire 3b and 3c gradually decrease and finally disappear, the coil 3 can maintain the bending ratio at a constant level. The number of pieces of wire in the coil 3 should be decided in a range where a black stripe, which is formed by the piece of wire 3a made of a radiopaque material, is practically effective when actually fluoroscoped. But the number should preferably be not more than six. In the coil 3 formed as described above, a tip of the piece of wire 3a, made of a radiopaque material, is fixed to the plug 4 in the distal section 2b of the shaft 2, upon which a base of the opposite side is fixed to the tapered section 2d of the shaft 2.

In FIG. 2, a portion 5 shadowed with inclined lines is a soldered connection filled in a gap formed between edge sections of pieces of wire 3b and 3c, each gradually decreasing, and the piece of wire 3a formed in a single-wire coil. Without this soldered connection 5, homogeneity in bending may be lost when inserted into a blood vessel, or blood may easily come into the coil 3, which may become a cause of thrombosis, but these problems can be solved by filling the soldered connection 5 in the gap. Also, by filling the solder connection 5 therein, the distal section 2b of the shaft 2 is soldered to the coil 3, so that the fixation between the coil 3 and the shaft 2 is more tightly and more safely performed.

Figure 3:
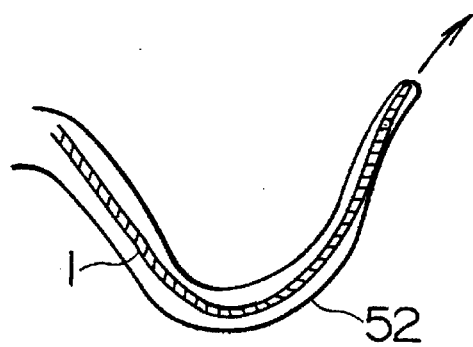
FIG. 3 is a drawing illustrating effect of a guide wire.

When the guide wire 1 having the configuration as described above is inserted into a blood vessel 52 having an extremely small curvature as shown in FIG. 3, the guide wire smoothly advances in a blood vessel 52 and passes through even a bending section. This is because the coil 3 has no connection like that in a conventional type of coil and the bending ratio thereof is maintained at a constant level. Also, in the guide wire 1, the piece of wire 3a for coil 3 made of a radiopaque material is shown under fluoroscopy with X-rays as a black section in the distal section and as spaced black stripes in the other section where the piece of wire 3a is coiled together with other pieces of wire 3b and 3c, so that an operator can quite easily distinguish the guide wire from the surrounding blood vessel 52. For this reason, the operator can recognize a bending section's positional relations in a stenosed section in the blood vessel 52 with the help of contrast media discharged from a catheter, and also can recognize the position of the guide wire 1 itself quite clearly.

Figure 1A:
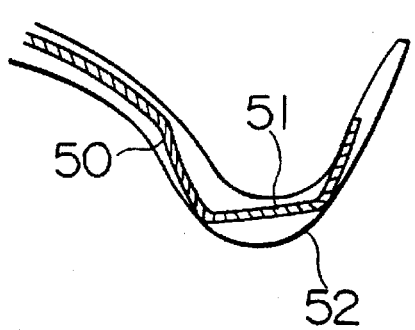
FIG. 1A and FIG. 1B are drawings each illustrating effect of a conventional type of guide wire.
Figure 1B:
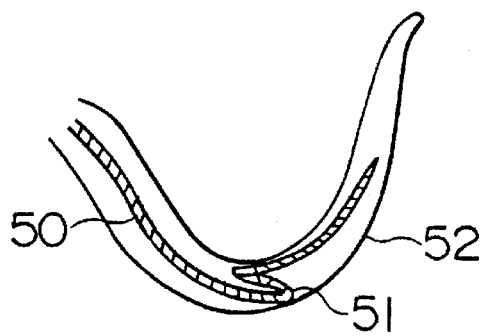

FIG. 4 is a drawing illustrating an example of another formation of the shaft, and the distal section 2b of this shaft 2 comprises two portions. Namely, a distal section $2b_1$ provided via a tapered section 2h of the cylindrical portion 2g forms a short section, and a cylindrical distal section $2b_2$ which is an independent body having almost the same length as that of the distal section 2b shown in FIG. 1 is jointed with and fixed to the distal section $2b_1$ in the axial direction. Other portions in this configuration are the same as those in FIG. 2.

FIG. 5 shows another embodiment of the present invention. In a guide wire 11 according to this embodiment, a coil 13 is a single-wire one consisting of one composite wire having no connection. A portion of the composite wire 15 constituting the coil 13 closer to the distal section 2b of the shaft 2 consists of a piece of wire 15a made of a material which is different from such a material as stainless steel and X-rays cannot pass through; namely in this case such a heavy metal as an alloy containing platinum as a main component, an alloy containing gold as a main component, an alloy containing tungsten as a main component, or lead, while a portion of the composite wire 15 other than the portion closer to the distal section 2b of the shaft 2 consists of a piece of wire 15b made of a material which has the same quality as stainless steel or the like or such a material as copper which can industrially be utilized and X-rays can pass through. Configuration in other portions of the shaft 2 is the same as that in the embodiment shown in FIG. 2. Also with this guide wire 11, the same effect as that with the guide wire 1 can be expected.

To manufacture the coil 13 as described above, as shown in FIG. 6, at first an edge section of the piece of wire 15a made of a radiopaque material is moved closer to an opposite edge section of piece of wire 15b made of a radio-transparent material (A). Both edge faces are contacted and fixed by means of welding, and then the metal thrusting toward the radial direction is removed to realize a smooth surface (B,C). Then the resulting composite wire consisting of pieces of wire 15a and 15b fixed together is pulled through a die 18 to obtain a composite wire having a smaller diameter, which is finished to a composite wire 15 having a necessary outer diameter (D,E). Outer diameter of the composite wire 15 is preferably in a range from 0.03 to 0.15 mm. Then by coiling the composite wire 15 manufactured as described above in the usual way, formed is the continuous and homogeneous coil 13 consisting of the composite wire 15, of which a portion is radiopaque (F).

Figure 7:
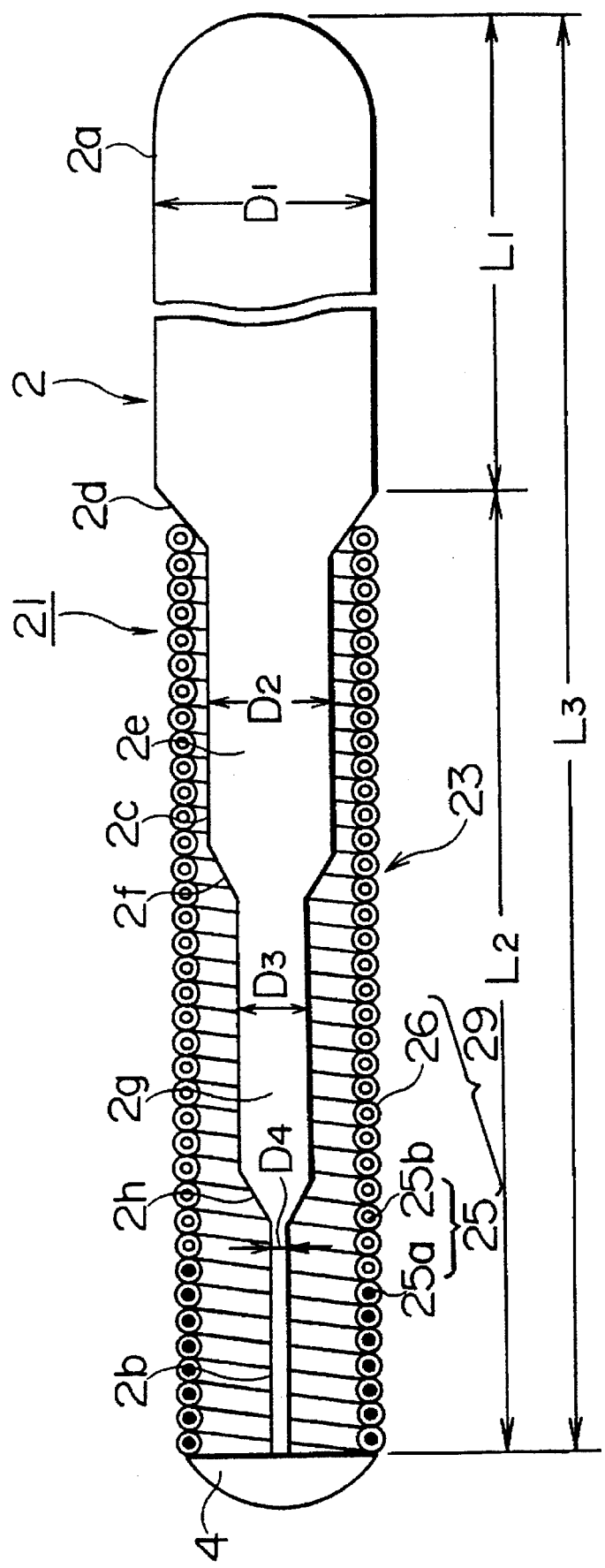
FIG. 7 is a longitudinal front sectional view of a guide wire illustrating a further different embodiment of the present invention.
Figure 8A:
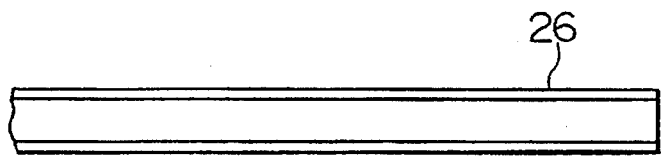
FIG. 8 is a schematic diagram illustrating a manufacturing process of the coil above.
Figure 8A:
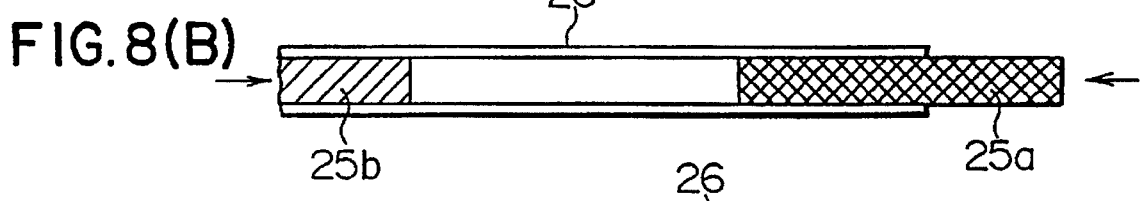
Figure 8A:
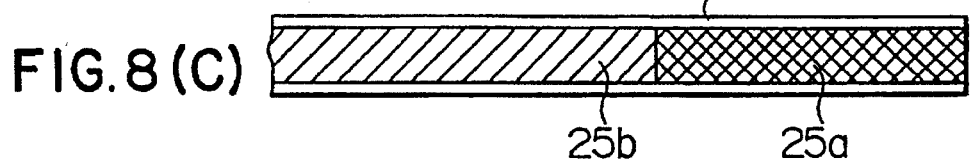
Figure 8A:
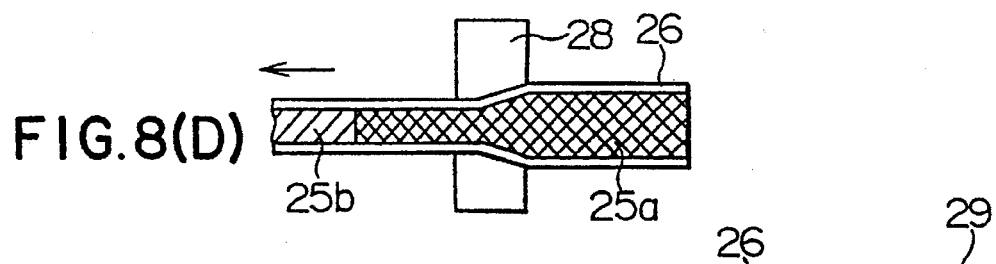
Figure 8A:
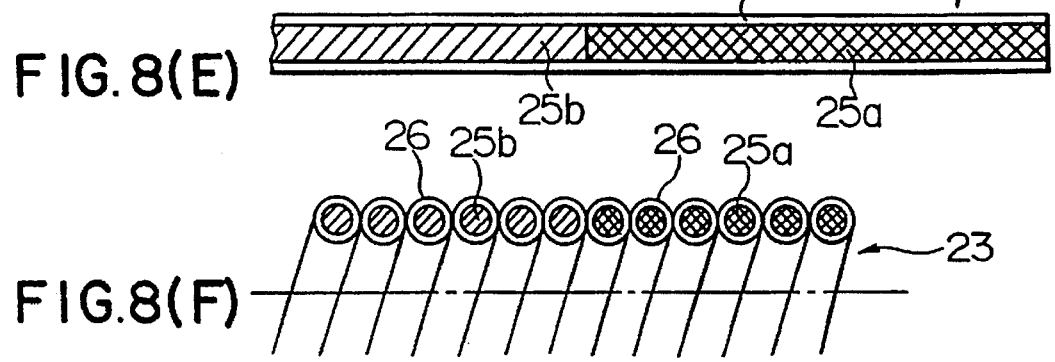

FIG. 7 shows a further different embodiment of the present invention. A composite wire 29 constituting a coil 23 of a guide wire 21 in this embodiment comprises an inner layer 25 and an outer layer 26. The outer layer 26 is made of such a material as stainless steel and has a tubular form, while a portion of the inner layer 25 closer to the distal section 2b of the shaft 2 is made of a material 25a which is different from such a material as stainless steel and X-rays cannot pass through; namely in this case such a material as an alloy containing platinum as a main component, an alloy containing gold as a main component, an alloy containing tungsten as a main component, or lead, while a portion of the inner layer 25 other than the portion closer to the distal section 2b of the shaft 2 is made of a material 25b which has the same quality as stainless steel or of a material like copper which can industrially be utilized and X-rays can pass through. Configuration of the shaft 2 in other portions is the same as that in the embodiment shown in FIG. 2.

To manufacture the coil 23 as described above, as shown in FIG. 8, at first the slender and tubular outer layer 26 is formed with such a material as stainless steel SUS 304 (A), and the piece of wire 25a made of such a metal or other radiopaque material as described above is inserted from one side of this outer layer 26. Also a piece of wire 25b made of a material which has the same quality as stainless steel or other material constituting the outer layer 26 or a radiotransparent material like copper which can industrially be utilized is inserted into the outer layer 26 from the other side thereof, and an edge face at the tip thereof is moved closer and contacted to that of the piece of wire 25a (B,C). Then, the complex layer comprising the outer layer 26 and the inner layer 25 formed as described above is pulled through a die 28 to obtain a composite wire having a smaller diameter, which is finished to a composite wire 29 having a necessary outer diameter (D,E). The outer diameter of the composite wire 29 is preferably in a range from 0.03 to 0.15 mm like in the embodiment shown in FIG. 5. Assuming that a cross-sectional area of the composite wire 29 in the portion with the wire 25a made of a radiopaque material is 1, it is preferable that a cross-sectional area of the piece of wire 25b made of a radiotransparent material and constituting the inner layer 25 is 0.2 or more. Then, by coiling the composite wire 29 formed as described above, the continuous and homogeneous coil 23, in which X-rays cannot pass through a portion of the inner layer 25, is formed as shown in (F).

In the configuration described above, the piece of wire 25b as the inner layer 25 made of radiotransparent material is not always necessary and the portion may be hollow. Furthermore, a radiotransparent material for the piece of wire 25b is not always limited to a metal, and non-metallic material such as powder of barium sulfate or bismuth oxide, or other substance in a solidified state may be used for that purpose. In the coil 23 formed as described above, the tip of the wire 25a made of a radiopaque material is fixed to the plug 4, while a proximal edge of the wire 25b made of a radiotransparent material is fixed to the tapered section 2d of the shaft 1.

Although details of the embodiments are not shown in FIG. 4 and FIG. 7, the distal section 2b of the shaft 2 may comprise two portions like in the embodiment shown in FIG. 4.

Although particular preferred embodiments of the present invention have been disclosed in detail for illustrative purposes, it will be recognized that variation or modification of the disclosed apparatus, including the rearrangement of part, lie within the scope of the present invention.

What is claimed is:

1. A method of producing a coil for a guide wire used for medical purposes, comprising steps of:

contacting and fixing an axial end of a piece of wire made of radiopaque material to an axial end of a piece of wire made of radiotransparent material by means of welding;

passing the connected pieces of wire through a die to form a composite wire having a smaller diameter; and winding the composite wire into a coil.

2. A method of producing a coil for a guide wire used for medical purposes, comprising the steps of:

inserting a piece of wire made of radiopaque material into a first end of a tubular sleeve made of radiotransparent material;

inserting a piece of wire made of radiotransparent material into a second end of the tubular sleeve;

passing the pieces of wire and tube assembly through a die to form a composite wire having a smaller diameter; and winding the composite wire into a coil.

* * * * *